United States Patent
Hajjar

[11] Patent Number: 5,575,656
[45] Date of Patent: Nov. 19, 1996

[54] METHOD AND APPARATUS FOR TOOTH RESTORATION

[76] Inventor: Victor J. Hajjar, 4800 Linglestown Rd., Harrisburg, Pa. 17112

[21] Appl. No.: 327,668

[22] Filed: Oct. 21, 1994

[51] Int. Cl.$^6$ .................................................. A61C 5/08
[52] U.S. Cl. .......................................... 433/219; 433/165
[58] Field of Search .................................. 433/165, 218, 433/219, 223, 166, 181, 183

[56] References Cited

U.S. PATENT DOCUMENTS

| | | | |
|---|---|---|---|
| 3,979,829 | 9/1976 | Lemos | 433/165 |
| 4,179,810 | 12/1979 | Kirsch | 433/165 X |
| 5,002,489 | 3/1991 | Fischer et al. | 433/219 X |
| 5,098,293 | 3/1992 | Lööf et al. | 433/165 |
| 5,284,442 | 2/1994 | Peterson | 433/223 |
| 5,366,374 | 11/1994 | Vlassis | 433/165 |

OTHER PUBLICATIONS

"Textbook of Operative Dentistry", Second Edition, Baum et al., W. B. Saunders Company, Philadelphia, PA, 1985, Table of Contents only.

"Tooth Preparation in Fixed Prosthesis" (Part 1), Weisgold et al., Continuing Education Article #1, vol. 1, No. 6, Nov./Dec. 1980, pp. 40–44; 46–47;50–55 & 81.

Primary Examiner—Christopher A. Bennett
Attorney, Agent, or Firm—Burns Doane Swecker & Mathis, LLP

[57] ABSTRACT

The present invention is directed to enhancing the accuracy with which tooth restorations are performed, including the manner by which a tooth is prepared and fit with a prosthetic crown. Further, the present invention is directed to reducing the skill dependent tasks associated with tooth restoration, while at the same time, improving the precision with which these procedures are performed. By improving the accuracy of restoration procedures, any need to repeat these procedures for a given patient can be eliminated and patient comfort can be improved.

19 Claims, 5 Drawing Sheets

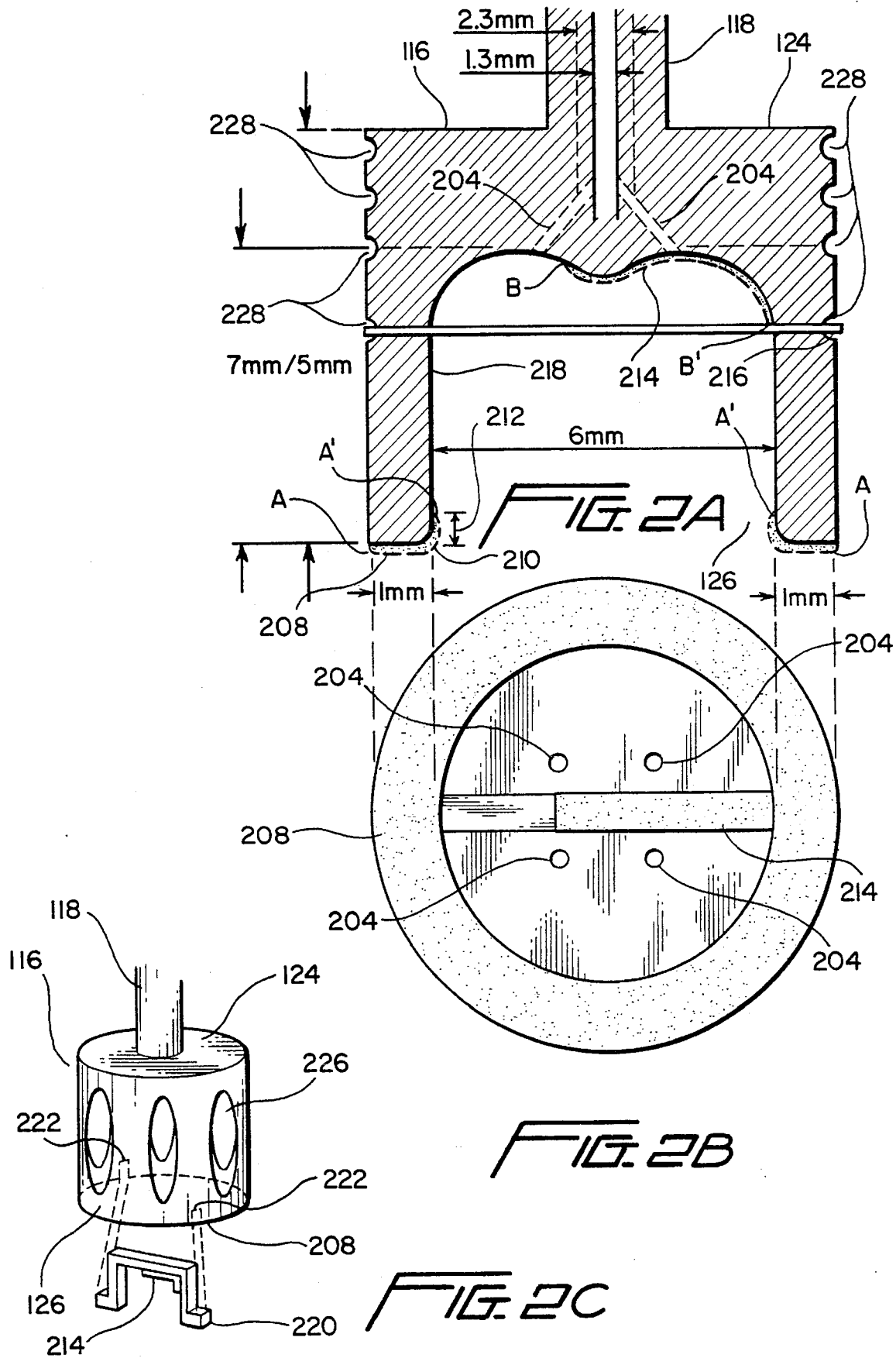

METHOD AND APPARATUS FOR TOOTH RESTORATION

BACKGROUND OF THE INVENTION

1. Field of the Invention

The present invention relates generally to the restoration of teeth, and more particularly, to methods and devices for improving the accuracy and simplifying the process of performing such restorations.

2. State of the Art

Presently, numerous methods exist for the restoration of teeth by dentists, including the use of artificial tooth material (such as gold or porcelain) to form a cast-restoration or a metal-ceramic restoration (i.e., prosthetic crowns). Prosthetic crowns are typically used to repair decayed tooth structure where support from the original tooth structure is either marginal, or unavailable.

Known techniques for preparing a tooth to receive a crown are susceptible to numerous variables, some of which are within the dentist's control and some of which are not; however all of these variables can detrimentally influence the accuracy with which: (1) the tooth is prepared to receive the crown; (2) the crown is prepared for placement on the tooth; and (3) the manner by which the crown is fit to and fixed on the prepared tooth.

For example, in preparing the original tooth to receive the crown, a dentist will typically use various shaped diamond burs in a high speed hand tool to remove approximately 2 mm of exterior tooth structure. The coronal portion of the tooth is shaped so that when the prosthetic crown is received from the laboratory, it will be of the approximate size and shape of the patient's original coronal portion prior to preparation. The skill of the dentist in manipulating the tool is critical. The dentist must accurately shape the tooth (e.g., retain tooth pulp) to ensure vitality. Further, the dentist must be careful to shape sidewalls of the tooth in a manner which will maximize retention; that is, only necessary portions of the tooth should be removed.

Because tooth preparation is performed totally by manipulation of a hand tool, and because the skill required for such tooth preparation will vary among dentists, the precision with which a tooth is prepared will vary widely. In some cases, too much tooth will be removed, thereby reducing retention or destroying vitality. In other cases, too little tooth will be removed, thereby requiring that the entire procedure be repeated, including preparation of a new crown.

The artistic ability of the dentist also plays a significant role in preparing the crown. That is, the prosthetic crown used to replace original tooth structure will vary in quality based on the skill on the dentist. Further, the quality of the prosthetic crown will vary based on the skill of the person who actually produces the crown (e.g., laboratory technician).

More particularly, after the patient's tooth has been shaped to receive the prosthetic crown, an accurate impression is formed from the prepared tooth. That is, an impression material is placed into the patient's mouth to form a negative impression of the prepared tooth. To accurately prepare the impression, all gingival bleeding must be stopped and the margin of the gum tissue must be retracted from the lower portion of the tooth. The impression material must then be properly injected into the sulcus area of the tooth. A tray which contains a combination of impression materials is then applied with pressure over the teeth in the area of the prepared tooth, including the prepared tooth.

Despite efforts by the dentist to obtain an accurate impression of the prepared tooth, many factors can detrimentally influence quality of the impression. For example, the characteristics of impression material vary widely. Further, the ability of the dentist to maintain a dry field of operation in the area of the prepared tooth can inhibit accuracy of the impression. The retraction of the gingival tissue can also effect the accuracy of the impression, as can the dentist's technique in obtaining the impression (i.e., the general care in obtaining an accurate impression).

Thus, the dentist's skill plays a significant role in accurate tooth restoration, both in preparing the tooth structure to receive the crown, and in obtaining the impression used to form the crown. While the precision with which these tasks are performed is largely within the dentist's control, many aspects of tooth restoration are not. For example, no matter how skilled the dentist, there are limits to the precision with which sidewalls of the tooth can be prepared. Ideally, to optimize retention, the sidewalls of the tooth should be parallel (i.e., orthogonal to the base of the tooth). However, even the most skilled dentist will prepare the tooth with sidewalls that are sloped on the order of fifteen (15) degrees, thereby removing excess tooth structure. Further, despite the talents of an extraordinarily skilled dentist, crown preparation is typically performed by a laboratory technician using the impression prepared by the dentist, and variables extant during crown preparation can degrade the quality and fit of the crown.

The typical laboratory procedure for crown preparation is as follows. Once the laboratory receives the impression from the dentist, the laboratory technician will set die pins in the impression and then form a master impression as a die (e.g., plaster models) of the patient's teeth. The technician will set the occlusal bite registration and articulate the models of the patient's teeth. Afterwards, the laboratory technician will saw the die to remove the tooth of interest, then trim the die of the tooth and mark the marginal finish line. The sub-structure is then waxed for preparation of the prosthetic crown.

After a wax pattern has been formed, it is converted into a casting (e.g., metal casting) to serve as a sub-structure (e.g., coping) of the crown. It is a challenge to produce a casting that will comply with acceptable tolerances, given the variables associated with the quality of the impression, the skill of the technician and the proper selection of die materials. Assuming that a satisfactory wax pattern has been prepared, the mold must be enlarged uniformly using known techniques of spruing and investing the wax pattern. After the investment is built up and hardened, the wax is burned out, followed by a complex casting technique necessary to prepare the sub-structure. Assuming accurate preparation of the casting alloy, the sub-structure is divested, sprue is removed and the finished sub-structure casting is prepared.

The casting is sand-blasted and steam-cleaned. The framework of the casting is degassed and an opaque primary coating is applied. A secondary opaque coating is applied followed by a porcelain build-up, with the build-up incorporating specific shading and color effects to assimilate the enamel of the original tooth. The porcelain build-up is then vacuum fired.

The combination of the cast sub-structure and porcelain build-up constitute the prosthetic crown. The final stages of crown preparation include a finishing of the porcelain build-up, after which the anatomy of the original tooth structure is carved therein. The porcelain crown is then glazed, and the cast interior of the crown is sand-blasted to remove external oxidation. The metal interior is then polished and the fit, shading and prosthetics of the crown are quality checked. The finished crown is then returned to the dentist for placement onto the prepared tooth structure.

The process of shipping the impression from the dentist to the laboratory technician, the preparation of the crown and the returning of the crown to the dentist typically involves a period of approximately two weeks. Upon receipt of the prosthetic crown from the laboratory, the dentist removes a temporary crown which had been placed over the prepared tooth of the patient following preparation of the impression. The permanent crown is then cemented into place. The dentist's skill is again called upon to ensure proper fit, occlusion bite registration and aesthetics of the prosthetic crown. While the dentist can modify the occlusion of the crown, inaccuracies in fit can require that a new crown be prepared and the entire process described above repeated, thus leading to increased time delays and patient discomfort (e.g., due to prolonged use of a temporary crown). In some cases, if the crown does not accurately fit, the dentist will use a bur to ground the interior; however, the use of a bur to shape the crown interior alters the fit and therefore detrimentally affects the marginal seal.

Conventional techniques for tooth restoration are described in the "Textbook of Operative Dentistry", Second Edition by Lloyd Baum et al, W. B. Saunders Company: 1985, Philadelphia, Pa. Further, conventional techniques for tooth preparation in conjunction with tooth restoration are described in the document entitled "Tooth Preparation in Fixed Prosthesis (Part I)" by Arnold S. Weisgold DDS et al, The Compendium of Continuing Education, Vol. I, No. 6, November/December 1980, pages 375–382 and pages 35–41, from the General Restorative Dentistry II, 1992, Course Component: Fixed Prosthodontics, Dr. Harold Baumgarten, et al.

In summary, conventional techniques for tooth restoration using prosthetic crowns are complex and are susceptible to substantial inaccuracies that stem from the skill level of the dentist and laboratory technician. These complexities and skill-dependent tasks translate into patient discomfort (due to improper fit) and increased costs. Further, the potential inaccuracies in tooth restoration can lead to crowns of relatively short life.

Thus, it would be desirable to improve the accuracy with which tooth restorations are performed. Further, it would be desirable to reduce the skill-dependent tasks associated with tooth restoration, and to reduce the cost associated with such procedures, without compromising the quality of these procedures.

SUMMARY OF THE INVENTION

Accordingly, the present invention is directed to enhancing the accuracy with which tooth restorations are performed, including the manner by which a tooth is prepared and fit with a prosthetic crown. Further, the present invention is directed to reducing the skill-dependent tasks associated with tooth restoration, while at the same time, improving the precision with which these procedures are performed. By improving the accuracy of restoration procedures, any need to repeat these procedures for a given patient can be eliminated and patient comfort can be improved.

Exemplary embodiments of the present invention are directed to methods and devices for improving the process of tooth restoration. Exemplary embodiments relate to a process for restoring a tooth comprising the steps of removing a first portion of the tooth to reduce exterior dimensions of the tooth; and removing a second portion of said tooth to form an exterior of said tooth into a predetermined shape for receiving artificial tooth material.

Further exemplary embodiments relate to an apparatus for shaping a tooth to receive artificial material, the apparatus comprising a cylindrically shaped housing having an open end; and a milling surface included in the housing, the housing and the milling surface being formed to mill sidewalls and an upper surface of the tooth into a predetermined shape for receiving artificial tooth material.

Further exemplary embodiments relate to an apparatus for shaping a tooth to receive an artificial tooth structure comprising, in combination: means for milling a tooth; and means for guiding said milling means, said guiding means being stabilized relative to said tooth such that said milling means forms the tooth into a predetermined shape.

Further exemplary embodiments relate to a process for forming an artificial tooth structure comprising the steps of: selecting predetermined dimensions for a sub-structure of the artificial tooth structure based on dimensions of a milling device; and forming said sub-structure with said predetermined dimensions, said sub-structure being formed to receive artificial tooth material.

BRIEF DESCRIPTION OF THE DRAWINGS

Other objects and advantages of the present invention will become more apparent from the following detailed description of the preferred embodiments when read in conjunction with the accompanying drawings, wherein like elements have been designated by like numerals, and wherein:

FIGS. 2A, 2B and 2C illustrate exemplary embodiments of a housing and milling surface which can be used in conjunction with the FIG. 1 combination;

DETAILED DESCRIPTION OF THE PREFERRED EMBODIMENTS

Figure 1:
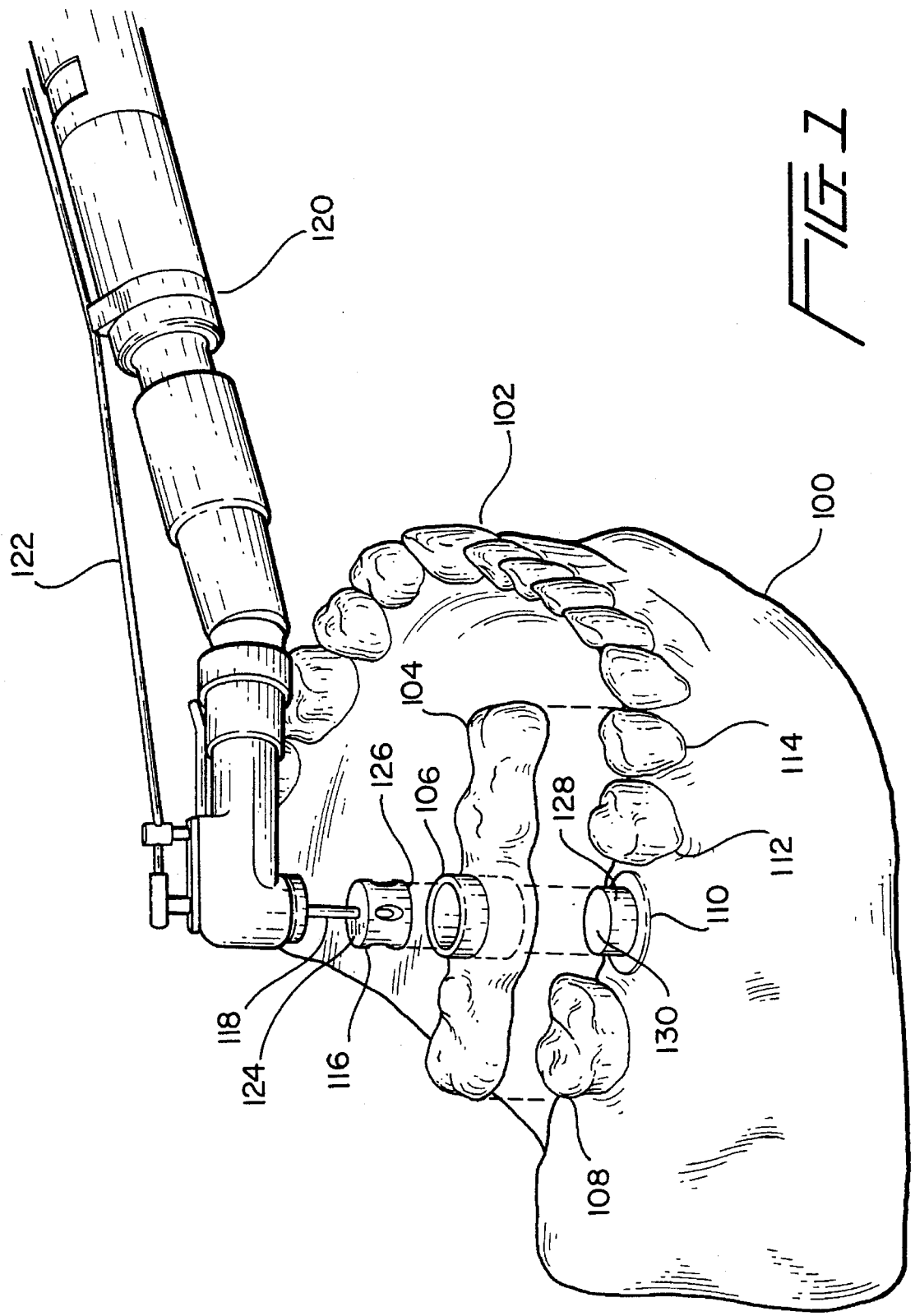
FIG. 1 illustrates an exemplary embodiment of a combination of components in accordance with an exemplary embodiment of the present invention.

FIG. 1 illustrates, in combination, an apparatus for shaping a tooth to receive an artificial tooth structure. In FIG. 1, a model replicating a patient's teeth is illustrated as including a lower half 100 of a set of dental models. The set of dental models can be formed with plaster in known fashion prior to any tooth preparation. Although the model illustrates a prepared tooth 110, such preparation would not, in accordance with the present invention, occur until a prosthetic crown had been prepared in accordance with exemplary embodiments to be described herein.

In accordance with an exemplary embodiment, a guiding means which includes a tooth template 104 having a drill guide 106 mounted therein, can be formed using the model.

The template can be formed by heating plastic over one or more teeth in the vicinity of the tooth to be prepared for restoration. In the exemplary FIG. 1 embodiment, the template 104 is formed by molding plastic over the teeth labeled 108, 110, 112, and 114. It will be appreciated that the template is formed prior to any preparation of the tooth 110 (i.e., the tooth which is to be restored).

After forming the plastic template 104, drill guide 106, which can be formed as a metal sleeve (e.g., stainless steel), is placed within and connected to the template 104. The metal sleeve can be fixed to the template using, for example, any known adhesive.

The template can be placed over the teeth 108–114 such that the metal sleeve surrounds the tooth to be restored. A milling surface of a drill can then be accurately guided over the tooth 110 which is to be restored. The template will stabilize the milling surface and control the angle with which the milling surface machines (i.e., mills) the tooth 110.

In the exemplary FIG. 1 embodiment, a milling means is provided which includes a milling surface in a housing which is cylindrically shaped and which includes a closed end 124. The milling surface is formed to mill sidewalls 128 and an upper surface 130 of the tooth 110 into the predetermined shape illustrated in FIG. 1 for receiving artificial tooth material, such as a prosthetic crown. The housing can be water cooled and has outer dimensions which are smaller than the inner dimensions of the drill guide 106. Thus, the housing can be lowered into the drill guide 106 to mill portions of the tooth 110.

The housing 116 can be attached to a hollow mandrel of a drill 120 via the closed end 124. The hollow mandrel provides a path for water supplied via a water line 122 of drill 120 to an interior of housing 116 during a milling operation. The drill and mandrel can be selected to provide low speed milling. The drill 120 can be of any known type, such as the contra angle drill model CAT. No. LX102-DI Latch Head with Internal Water Spray for Implants, available from MTI Precision Products, in Lakewood, N.J.

While the tooth 110 to be prepared is illustrated as an inside molar in the FIG. 1 embodiment, those skilled in the art will appreciate that any tooth could be prepared to receive a crown. In each case, the template must be formed of sufficient size to ensure stable milling operations. For example, there is no tooth to the left of the tooth 108. Thus, to mill tooth 108, a template can be formed over the entire lower half of the FIG. 1 model so that the drill guide 106 will properly stabilize the housing 116.

In addition, those skilled in the art will appreciate that while exemplary embodiments as described herein can be used to prepare a single crown, the present invention can be used in conjunction with almost any restoration. For example, exemplary embodiments are also applicable to bridge preparation using, for example, two drill guides on a template formed using the same dental model. Alternately, multiple drilling guides fabricated by using the same model can be formed in separate templates.

Because the housing 116 is formed with outer dimensions that are smaller than the inner dimensions of the drill guide 106, the milling blade housing can be lowered through the drill guide 106 once the template has been placed onto the tooth to be prepared. In exemplary embodiments, the interior of the drill guide 106 and/or the exterior of housing 116 can be lubricated (e.g., silicone coated).

As illustrated in FIG. 1 and as described previously, the template 104 and the drill guide 106 can be formed as an integral unit. In the alternate embodiments, this integral unit can be formed of a single material, with the key criteria being an ability to stabilize the milling housing 116 during a drilling operation.

Referring to FIGS. 2A–2C, the housing 116 can be seen in greater detail. The closed end 124 of the cylindrically shaped housing receives the hollow mandrel 118. Water can be supplied through the mandrel 118 to water outlets 204 that communicate with an interior of the housing 116. The wall of an open end 126 of the housing, which is opposite the closed end 124, is circular and approximately 1 mm in width. The open end has an exemplary external diameter of, for example, 8 mm and an exemplary inner diameter of 6 mm.

The open end 126 of the cylindrically shaped housing includes a milling surface formed as a cutting edge along the entire periphery of the open end. This cutting edge is designated 208, and can be seen to extend from an outer edge of the open end 126 to an interior area 212, along the cross-sectional path A–A'. The interior edge 210 of the open end 126 is curved to avoid creating a sharp edge in the tooth which is to be prepared.

As seen in FIGS. 2A and 2B, the milling surface can also include a second cutting edge 214 along at least a portion of the closed end 124, within the housing interior, along the path B–B' (i.e., from a point B located to one side of the mandrel 118, across the closed end 126, and down a portion of an interior sidewall of housing 116 to point B'). Those skilled in the art will appreciate that the cutting edge along the periphery of the cylindrically shaped housing will mill sidewalls 128 of the tooth 110 (FIG. 1), while the cutting edge 214 which extends along the distance B–B' in FIG. 2A will mill the upper surface 130 of tooth 110 (FIG. 1).

During the entire milling process, water is supplied through the water outlets to cool the milling surface. A vertical height of the housing (i.e., from the open end 126 to the closed end 124) can be on the order of approximately 7 mm, while a distance from the open end of the housing to the interior cutting edge 214 can be on the order of 5 mm. The hollow mandrel 118 can have a diameter of approximately 2.3 mm, with an interior water supply (that is, the hollow interior) having a circular cross-section with a diameter of approximately 1.3 mm.

FIG. 2B illustrates a bottom view of the housing 116. As illustrated in FIG. 2B, cutting edges can be seen to exist along the periphery of the open end 126. Further, cutting edge 214 can be seen to extend across slightly greater than ½ of the closed end 124, within the interior of the cylindrically shaped housing. Further, the water outlets can be seen in FIG. 2B.

FIG. 2C illustrates elliptically shaped holes 226 spaced around the cylindrically shaped housing. These holes permit water and milled tooth debris to escape during a drilling operation.

As illustrated in FIG. 2A, the housing 116 can be seen to include an adjustable stop 216. The adjustable stop can be placed, rotated (e.g., on threads) or slid (e.g., spring biased) along an exterior of the housing. The adjustable stop can be raised or lowered along an exterior periphery of the housing. The adjustable stop 216 thus represents a means for limiting a depth to which the tooth 110 (FIG. 1) will be milled. In operation, the adjustable stop of the limiting means abuts, for example, an upper surface of the guiding means (e.g., an upper edge of the drill guide 106) to limit the depth to which the milling blade 116 can be lowered into the drill guide 106. The use of this stop will prevent overdrilling of the tooth 110. Thus, grooves 228 located on the periphery of the housing constitute means for adjusting the depth to which the tooth will be milled.

In alternate embodiments, the adjustable stop can be eliminated or replaced with markings that indicate varying depths of cut. For example, the periphery of the housing can include plural markings vertically spaced from one another on the housing by predetermined increments (e.g., 1 mm increments). When a selected marking is parallel with an upper edge of the drill guide, milling of the tooth can be discontinued. The markings can be labelled to, for example, identify the depth of cut which will result when the marking is parallel with the upper edge of the drill guide.

Those skilled in the art will appreciate that the more parallel the walls of the prepared tooth, the greater the retention will be, and the less the amount of tooth which needs to be milled. In accordance with exemplary embodiments, interior walls 218 of the FIG. 2A housing can be formed parallel (i.e., at ninety degrees relative to the closed end 124). Alternately, the walls 218 can be formed at angles with slopes that range from approximately zero degrees (relative to a normal line through the closed end) up to, for example, six degrees so that when the tooth is milled, its diameter will increase from the top of the tooth toward the gingival margin. Those skilled in the art will appreciate that a slope of six degrees or less is far below the typical slope (e.g., fifteen degrees) achieved when a tooth is prepared by hand, using conventional techniques.

Thus, exemplary embodiments of the present invention can substantially improve retention by preparing a tooth into a predetermined shape having predetermined dimensions (i.e., predetermined side wall angle and height). The present invention permits a substantial portion of the original tooth structure to be retained, thereby adding strength to the tooth once the prosthetic crown has been cemented into place.

Those skilled in the art will also appreciate that the milling surface of the housing can be any of a variety of materials. For example, the milling surface can be diamond, porcelain, any hard metal, sand, or any other material which can provide an abrasive surface for cutting. In addition, while the specific embodiment illustrated in FIG. 2A includes a cutting edge as the milling surface, those skilled in the art will appreciate that any cutting surface, including a sawtooth edge, can also be used.

In addition, those skilled in the art will appreciate that while the cutting edges have been described as being integral within the housing 116, a separate insert 220 (FIG. 2C) can be used to form the second cutting edge 214. In such an embodiment, the cylindrically shaped housing can be formed with an exterior periphery having the first cutting edge 208 (e.g., diamond cutting surface). Slots 222 can then be located along sides of the cylindrically shaped housing for receiving the insert 220 having the upper cutting edge 214 formed thereon. The insert 220 fits into the slots of the cylindrically shaped housing to provide a two part housing. Differently sized inserts can be used to control the height to which the tooth is milled (i.e., in place of, or in conjunction with, the adjustable stop 216 of FIG. 2A).

Having described exemplary embodiments of a structure for preparing a tooth in accordance with the present invention, a process by which a tooth can be prepared will now be described. Prior to any drilling of a patient's tooth, a set of dental models (e.g., plaster models) can be prepared and used to select predetermined dimensions for a sub-structure of the artificial tooth structure. With these predetermined dimensions, a sub-structure can be selected that is matched in size to a housing which will be used to mill the tooth. The sub-structure can be a pre-formed coping which will be used for preparing the prosthetic crown.

The preparation of the crown can be performed in either the dentist's office or can be sent to a laboratory for preparation. For purposes of the following discussion, it will be presumed that the set of dental models have been sent to a laboratory where upon receipt, the laboratory technician will select a standardized housing appropriate for the tooth size to be restored.

In sending the set of models to the laboratory, the dentist can also send information regarding appropriate dimensions for the housing and/or the milling of the tooth based on a review of X-rays of the patient's tooth. The laboratory can prepare the template 104 with the drill guide 106, the drill guide 106 being selected based on the size of the drill housing selected. Then, after selecting an appropriate housing, a pre-formed coping matched in shape to the housing can be selected as a sub-structure for the prosthetic crown.

Thus, without the use of any impressions of a prepared tooth, and in fact, before the patient's tooth has even been operated upon, the laboratory can select a pre-formed, machined coping as a sub-structure for the prosthetic crown. The pre-formed coping can be formed of, for example, any conventional material such as metal or porcelain.

Additional porcelain can then be built-up on the coping. The porcelain which is built-up on the coping can be finished and carved to correspond to the anatomy of the tooth to be restored. For this purpose, the laboratory can articulate the set of dental models and attempt to carve the external crown anatomy to match the original tooth structure and bite registration. The porcelain crown then can be glazed. If the coping is formed of metal, any exposed metal can be sand-blasted subsequent to build-up of the crown to remove oxidation. Afterward, the crown can be polished. The finished crown can then be returned to the dentist with the set of dental models, the template 104 with drill guide 106, and the milling blade housing 116.

Upon receipt of the dental models, the template with drill guide, the housing 116 and the crown, the dentist can test the fit of the crown on the plaster dental models. The dentist can prepare the tooth 110 of the lower dental model 100 (FIG. 1) to receive the crown. This test fit can occur before the patient ever returns to the dentist's office.

That is, the dentist can begin the tooth restoration process by performing a rough milling of the plaster tooth. The dentist can use a conventional drill to remove approximately 2 mm of the selected tooth to be restored on the dental model. No drilling within the patient's mouth is performed at this time. After removing approximately 2 mm of the selected tooth on the dental models, the dentist places the template with the drill guide onto the dental model. The dentist next attaches the housing 116 to the drill 120 as illustrated in FIG. 1. The drill, with the attached housing, is then lowered into the drill guide 106 to remove a portion of the selected tooth 110 on the articulated model, and to mill this tooth into a predetermined shape for receiving artificial tooth material (i.e., the prosthetic crown). The crown can then be placed on the prepared tooth of the model and its fit can be examined.

Once the dentist is assured that the housing 116 and milling surface will properly prepare the tooth for receipt of the crown, the patient can be contacted to return to the dentist's office. Upon return, the dentist can now prepare the patient's tooth for restoration in the same manner that the dental model was prepared to test the crown's fit. That is, the dentist can first remove a portion of the selected tooth to reduce exterior dimensions of the tooth. To this end, the dentist can remove approximately 1–2 mm of the hard enamel on the patient's tooth. After removing the external hard enamel, the dentist can use the housing 116 to remove a second portion of the tooth to form the tooth into a predetermined shape for receiving the prosthetic crown.

Because the dentist has already checked the fit of the crown using the dental models, the dentist can be certain that the prepared tooth of the patient will properly receive the prosthetic crown and that a proper fit will result. That is, the template 104 and drill guide 106 will provide an accurate alignment of the milling blade housing with the tooth 110 so that milling of the tooth 110 is performed in exactly the same manner as it was intended to be prepared by the laboratory which prepared the housing 116 and the prosthetic crown. The drill guide 106 is formed at a predetermined angle and integrated with the template 104 so that the angle with which the tooth 110 is milled will be accurately controlled.

Having prepared the tooth for receipt of the prosthetic crown, the dentist can then place the prosthetic crown onto the prepared tooth. After checking the fit, the dentist can remove the prosthetic crown and apply any conventional adhesive to the tooth and/or interior of the prosthetic crown. The crown can then be placed onto the prepared tooth and cemented onto place. Afterward, the dentist can fine tune the exterior anatomy of the crown to ensure a comfortable fit for the patient and to make any necessary marginal corrections.

Figures 3A, 3B:
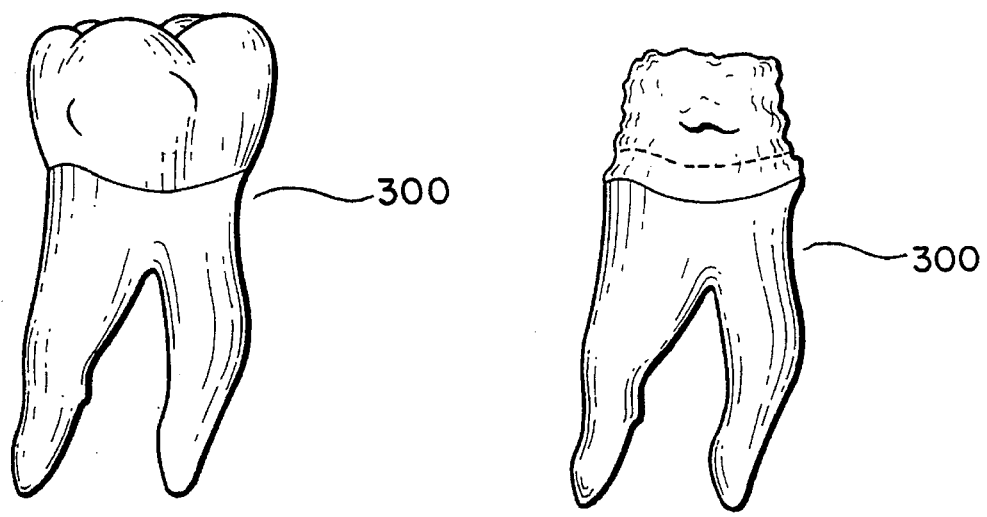
FIGS. 3A–3C illustrate a tooth prior to preparation, subsequent to a rough preparation and subsequent to final preparation for receiving a prosthetic crown in accordance with an exemplary embodiment of the present invention.
Figure 3C:
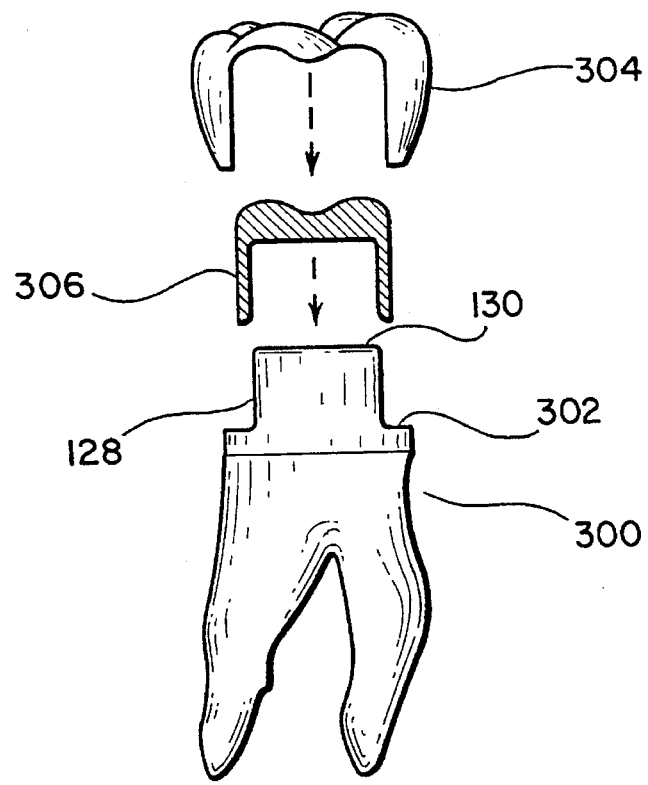

FIG. 3A illustrates a tooth 300 prior to any preparation. FIG. 3B represents a rough drilling of the tooth to remove approximately 1–2 mm of hard enamel, and to provide room within the patient's mouth to receive the drill guide 106 and the housing 116 around the tooth perimeter. FIG. 3C illustrates the tooth after it has been prepared using the housing 116.

As can be seen in FIG. 3C, the curved portion 210 of the cutting edge 208 in FIG. 2A results in a curved transition between the tooth base 302 and the remaining sidewalls 128 of the milled tooth. The base 302, in accordance with the exemplary milling surface of FIG. 2A, has a width of approximately 1 mm to accommodate a porcelain crown 304 formed with a thickness of at least 1 mm at its thinnest point. The crown 304 is built-up on a pre-formed sub-structure 306 having a predetermined dimensions (i.e., dimensions which are a function of the housing used to mill the tooth 300, and not a function of a previously prepared tooth from which an impression was created). As illustrated in FIG. 3C, sidewalls 128 of the prepared tooth are approximately parallel, thus ensuring a high level of retention.

Those skilled in the art will appreciate the precision which exemplary embodiments of the present invention can provide. For example, the present invention eliminates any need to prepare a patient's tooth prior to preparation of a crown. Further, the present invention eliminates any need for an impression of a prepared tooth, thereby eliminating any inaccuracies associated with such preparation. Contrary to conventional practice whereby an impression of a prepared tooth is used to form a casting, exemplary embodiments can use a pre-formed, machined sub-structure; the complex process associated with forming a cast crown is thereby eliminated.

Further, exemplary embodiments of the present invention eliminate the inaccuracies in tooth preparation which can result in too much or too little tooth being removed, and which can result in increased side wall angles that can degrade retention and inhibit proper sealing of the crown.

Accordingly, exemplary embodiments provide a more accurate fit of the prosthetic crown, resulting in longer lasting fits which are less susceptible to saliva and other contaminate infiltration.

Those skilled in the art will appreciate that, because teeth will vary in size from one patient to another, some variation in the housing size will be necessary to accommodate different teeth. Accordingly, exemplary embodiments of the present invention can include a set of milling blade housings which will accommodate any size tooth for typical patients. For example, FIGS. 4A–4E illustrate a set of five housings, with integral milling surfaces, for accommodating most teeth. Each of the housings in FIG. 4 can be formed in a fashion similar to that described with respect to FIG. 2. However, dimensions of the housings can be altered to accommodate different teeth size.

Figure 4A:
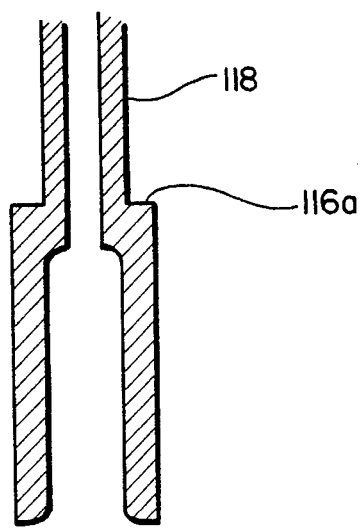
FIGS. 4A–4E illustrate differently sized milling housings which can be used to accommodate differently size teeth.
Figure 4B:
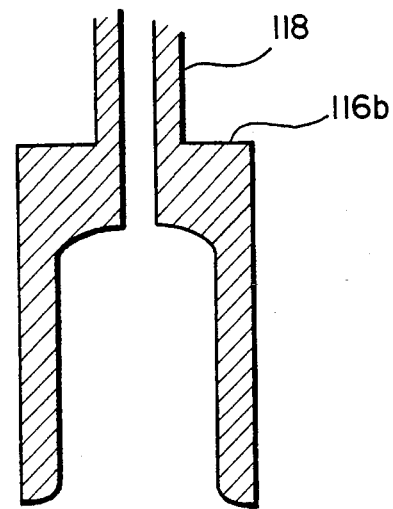
Figure 4C:
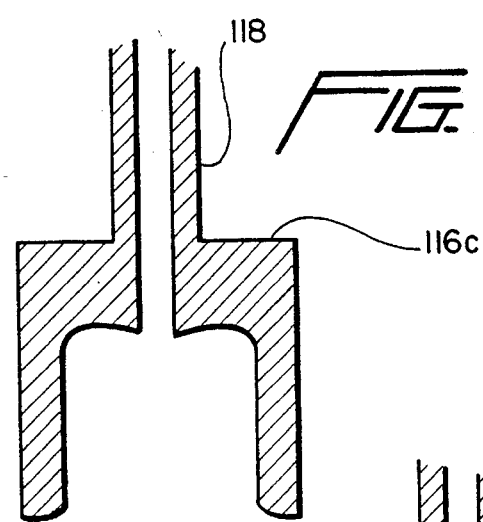
Figure 4D:
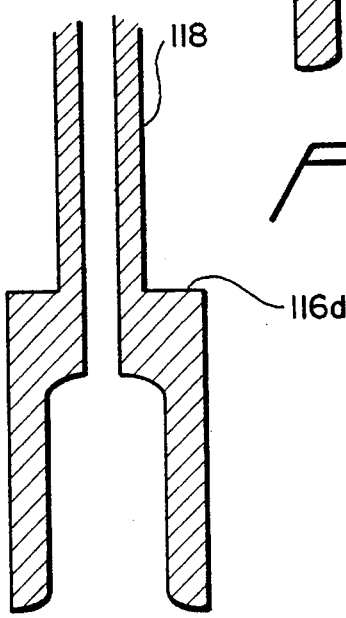

For example, the milling blade housing of FIG. 4A formed with an interior vertical dimension of 7 mm, a cutting edge of approximately 1 mm, and an inner diameter of approximately 2 mm can be used for the centrals, while that of FIG. 4D can be used for the lateral cuspid, the first biscupid and the second biscupid. As illustrated, the interior vertical dimension of the FIG. 4D housing is approximately 6 mm, while the width of the cutting edge at the periphery of the cylindrical shaped housing is approximately 1 mm and the inner diameter is approximately 3 mm. In all embodiments, the second edge (e.g., edge 214) can also be formed with a width of approximately 1 mm.

Figure 4E:
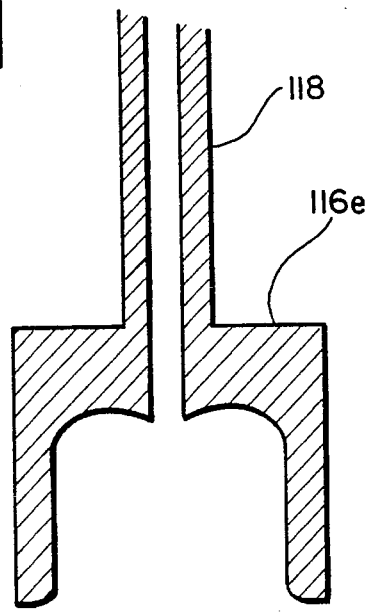

FIG. 4B illustrates a housing suitable for central teeth, wherein the interior vertical dimension is approximately 7 mm, the peripheral cutting edge of the cylindrically shaped housing is approximately 1 mm and the inner diameter is approximately 4 mm. FIG. 4C shows an exemplary housing for the second molar, wherein the vertical interior dimension is approximately 5 mm, the exterior peripheral cutting surface is approximately 1 mm and the inner diameter is approximately 5 mm. FIG. 4E illustrates an exemplary embodiment of a housing for the first molar and the second molar, with the interior vertical dimension being approximately 5 mm, with the peripheral cutting surface being approximately 1 mm in width and with the inner diameter being approximately 6 mm.

Those skilled in the art will appreciate that additional sized housings can be added as necessary to accommodate specific situations. However, regardless of the exact size of the housing selected, a pre-formed coping can be machined at the time the housing is prepared (i.e., prior to tooth preparation), with the two being sized accordingly so that an accurate fit of the coping to a tooth which has been milled using the housing can be achieved.

FIG. 3C illustrates an exemplary embodiment of a cross-sectional slice of a machined coping 306 which has been pre-formed relative to the size of a housing which will be used to machine the patient's tooth. The coping 306 is, of course, formed to completely surround the walls 128 and top surface 130 of the milled tooth. Similarly, the crown build-up 304 which is formed on the coping 306 is shown as a cross-sectional slice, and would completely surround the coping 306 in practice. Given that the pre-formed coping can be machined beforehand, many of the conventional steps associated with crown preparation are eliminated. In fact, because the coping constitutes a pre-formed sub-structure, the only steps of conventional crown preparation which need be implemented are those of building-up porcelain on the coping, finishing the porcelain and glazing the porcelain.

Because much of the time associated with preparation of an impression, tooth preparation and crown preparation can be eliminated in accordance with exemplary embodiments of the present invention, the overall time associated with tooth restoration can be substantially reduced. Thus, the costs associated with tooth restoration can be reduced, yet the precision and comfort of fit associated with the prosthetic crown can be substantially enhanced.

Figure 5A:
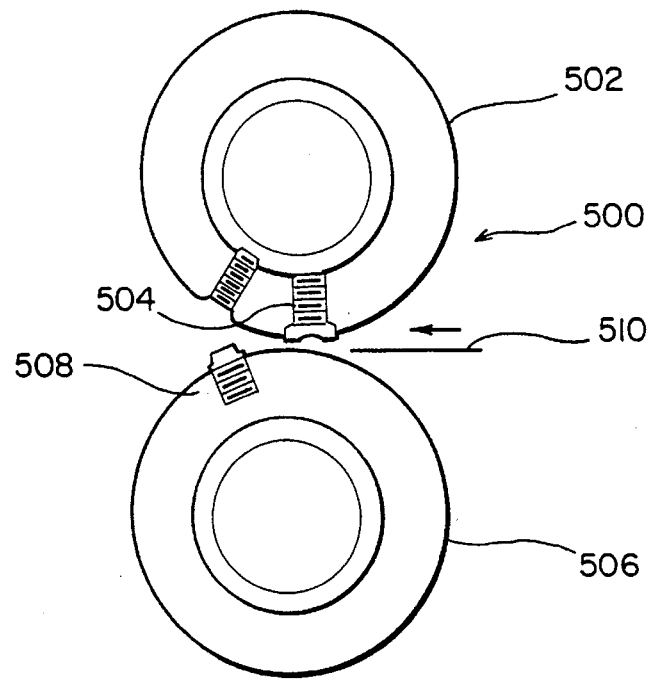
FIGS. 5A–5B illustrate an exemplary process for forming a coping in accordance with an exemplary embodiment.

FIG. 5A illustrates one exemplary embodiment of an apparatus and method for machining a coping from metal. In the exemplary FIG. 5A embodiment, a machine 500 can be formed with a circular structure 502 having plural dies 504 located about its periphery. The dies 504 can be formed as receptacles that form copings to predetermined dimensions. A cooperative structure 506, which can be rotated with the structure 502, includes a plurality of dies 508 formed as counterparts to the receptacles 504. A sheet of metal 510, from which a coping is to be machined, is drawn or fed between the structures 502 and 506. In operation, as the sheet of metal is located beneath a receptacle 504, a counterpart die 508 is used to punch the metal and form the coping within the receptacle 504.

Figure 5B:
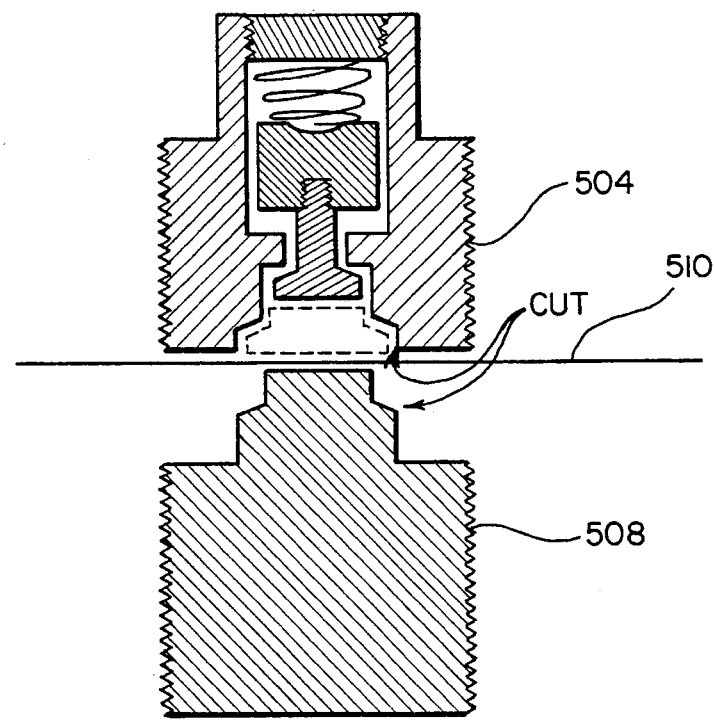

Referring to FIG. 5B, a partial cross-section of a single die is illustrated with the metal sheet 510 located therebetween. In operation, a portion of either or both the receptacle 504 and the die 508 are moved relative to one another in conventional fashion to shape the metal sheet into a coping of predetermined size, with blades on the die 508 cutting edges of the coping. Because a plurality of the dies can be included in the FIG. 5A structure, multiple copings of predetermined size can be formed in rapid fashion. Again, because the copings are formed to predetermined sizes, that they can be mass produced in this fashion.

While the exemplary embodiment for machining a coping as illustrated in FIGS. 5A and 5B constitutes one way of forming multiple copings in relatively rapid fashion, those skilled in the art will appreciate that numerous methods can be used for machining the copings. For example, any type of machining which can accurately form metal will be appropriate. Further, those skilled in the art will appreciate that in lieu of machining the copings, molds can be formed to predetermined dimensions, and then used to form the copings from porcelain or any other formable material. In such cases, numerous molds formed to the same predetermined dimensions can be used to mass produce the porcelain copings. Regardless of the manner in which the copings are formed to predetermined dimensions, such copings can be built-up in known fashion to produce the prosthetic crown.

Those skilled in the art will appreciate that the exemplary embodiments described above are by way of illustration only, and modifications will be readily apparent. For example, in lieu of providing an adjustable stop to control vertical displacement of the housing 116 within the drill guide 106, a plastic stop can be formed on the housing 116 to limit vertical movement within the drill guide 106. Alternately, any use of a stop can be eliminated, and vertical drilling can be regulated by the dentist's own hand control and sense of feeling, or via the use of markings on the housing exterior.

Further, those skilled in the art will appreciate that the housing 116 can be formed of materials (e.g., stainless steel) suitable for sterilization and reuse. Alternately, the housings can be used a single time and then disposed. In the latter case, it may be desirable to include a fixed stop, rather than an adjustable stop to minimize cost of the disposable housing.

As mentioned above, the housing 116 can be formed of any metal, such as stainless steel. Alternately, any material suitable for use in the industry, such as porcelain, can be used. As mentioned previously, the housing size must be set in accordance with the size of the drill guide 106. For example, a very tight tolerance between the external dimensions of the housing 116 and the inner dimensions of the drill guide 106 can be used (e.g., on the order of 10 microns). Further, those skilled in the art will appreciate that the interior of the sub-structure used as the coping for the prosthetic crown should be formed slightly larger than the size of the prepared tooth upon which the crown is to be placed. For example, the sub-structure should be formed with a diameter approximately 0.1 mm larger than that of the prepared tooth upon which the crown is to be placed.

Once the prosthetic crown has been formed, and the tooth upon which the crown is to be placed has been prepared, the crown can be inserted into place. In accordance with exemplary embodiments, any technique used for cementing a crown into place can be used in accordance with exemplary embodiments of the present invention. For example, a light cured cement can be used whereby the crown is inserted into place and, after all adjustments have been made, is exposed to a relatively high intensity light to cure the cement. In addition, known techniques which improve seating of the crown can be used, including techniques whereby small holes are inserted into the top of the crown to allow cement to be released therefrom during placement of the crown on the prepared tooth. In accordance with exemplary embodiments, a drill speed on the order of 300 to 600 revolutions per minute can be used to mill the relatively soft tooth portion beneath the enamel. However, in accordance with exemplary embodiments, any drill suitable for machining teeth can be used, and the invention is not limited to the specific drill mentioned above.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A process for restoring a tooth comprising the steps of:
   removing a first portion of said tooth to reduce exterior dimensions of the tooth; and
   removing a second portion of said tooth to form an interior of said tooth into a predetermined shape for receiving artificial tooth material wherein said step of removing said second portion further includes steps of:
   placing a tooth template having a drill guide mounted thereon over said tooth; and
   lowering a milling blade through said drill guide to remove said second portion, said milling blade having predetermined dimensions for forming said predetermined shape.

2. A process according to claim 1, further comprising the step:
   performing said steps of removing first and second portions on a model prior to removing any of said tooth.

3. A process according to claim 1, further comprising the steps of:
   placing a pre-formed sub-structure onto said tooth, said pre-formed sub-structure having predetermined dimensions matched to said predetermined shape.

4. A process according to claim 1, further comprising the step of:

forming said tooth template and said drill guide as an integral unit.

5. Apparatus for shaping a tooth to receive artificial material, said apparatus comprising:

a cylindrically shaped housing having an open end;

a milling surface included in said housing, said housing and said milling surface being formed to mill sidewalls and an upper surface of said tooth into a predetermined shape for receiving artificial tooth material; and means, located on an exterior of said housing, for limiting a depth to which said tooth is milled.

6. Apparatus according to claim 5, wherein the milling surface further includes:

a first cutting edge along a periphery of said open end.

7. Apparatus according to claim 6, wherein said housing further includes:

a closed end opposite said open end, and wherein said milling surface also includes a second cutting edge formed along at least a portion of said closed end within said housing.

8. Apparatus according to claim 7, wherein said first cutting edge and said second cutting edge are formed integral with said housing.

9. An apparatus for shaping a tooth to receive an artificial tooth structure comprising, in combination:

means for milling a tooth; and means for guiding said milling means and for stabilizing said milling means relative to said tooth such that said milling means forms the tooth into a predetermined shape, wherein said milling means further includes:

means for limiting a depth to which said tooth is milled, said limiting means including a stop for abutting a surface of said guiding means.

10. The combination according to claim 9, wherein said predetermined shape includes a predetermined side wall angle of said tooth.

11. The combination according to claim 9, wherein said limiting means further includes:

means for adjusting said depth to which said tooth is milled.

12. The combination according to claim 9, wherein said guiding means further includes:

a plastic template formed using an articulated set of dental models, said plastic template being formed with a sleeve mounted thereon for receiving said milling means.

13. Apparatus according to claim 12, wherein said template and said sleeve are formed as an integral unit.

14. The combination according to claim 9, wherein said milling means further includes:

a water cooled housing having a milling surface formed integrally therewith, said housing having external dimensions suitable for movement of said housing within said guiding means.

15. Process for shaping a tooth to receive an artificial tooth structure comprising the steps of:

selecting predetermined dimensions for a sub-structure of the artificial tooth structure based upon dimensions of a milling device;

forming said sub-structure with said predetermined dimensions, said sub-structure being formed to receive artificial tooth material; and guiding said milling device and stabilizing said milling device relative to said tooth such that said milling device forms the tooth into a predetermined shape which corresponds to said predetermined dimensions, said step of guiding and stabilizing further including a step of:

limiting a depth to which said tooth is milled by using a stop which abuts a surface of a guide.

16. Process according to claim 15 further comprising the step of:

applying said artificial tooth material to said sub-structure to form the artificial tooth structure.

17. Process according to claim 15, wherein said step of forming further includes the step of:

machining said sub-structure to said predetermined dimensions using a die.

18. An apparatus for shaping a tooth to receive an artificial tooth structure comprising, in combination:

means for milling a tooth; and means for guiding said milling means and for stabilizing said milling means relative to said tooth such that said milling means forms the tooth into a predetermined shape, wherein said guiding means further includes:

a plastic template formed using an articulated set of dental models, said plastic template being formed with a sleeve mounted thereon for receiving said milling means.

19. Apparatus according to claim 18, wherein said template and said sleeve are formed as an integral unit.

* * * * *